United States Patent
Hanzawa et al.

(10) Patent No.: US 9,952,213 B2
(45) Date of Patent: Apr. 24, 2018

(54) METHOD FOR EVALUATING ISCHEMIC HEART DISEASE BY ASSAYING COMPLEMENT FACTOR H OR D

(71) Applicant: HITACHI, LTD., Tokyo (JP)

(72) Inventors: Hiroko Hanzawa, Tokyo (JP); Takeshi Sakamoto, Tokyo (JP); Yuji Kuge, Hokkaido (JP)

(73) Assignee: HITACHI, LTD., Tokyo (JP)

( * ) Notice: Subject to any disclaimer, the term of this patent is extended or adjusted under 35 U.S.C. 154(b) by 61 days.

(21) Appl. No.: 14/514,523

(22) Filed: Oct. 15, 2014

(65) Prior Publication Data

US 2015/0105291 A1 Apr. 16, 2015

(30) Foreign Application Priority Data

Oct. 15, 2013 (JP) .................................. 2013-214455

(51) Int. Cl.
| | |
|---|---|
| *G01N 33/50* | (2006.01) |
| *G01N 33/53* | (2006.01) |
| *A61P 9/10* | (2006.01) |
| *G01N 33/564* | (2006.01) |
| *C07K 14/47* | (2006.01) |
| *C07K 14/745* | (2006.01) |
| *C07K 16/36* | (2006.01) |

(52) U.S. Cl.
CPC .............. *G01N 33/564* (2013.01); *A61P 9/10* (2018.01); *G01N 33/50* (2013.01); *G01N 33/53* (2013.01); *C07K 14/472* (2013.01); *C07K 14/745* (2013.01); *C07K 16/36* (2013.01); *G01N 2333/4716* (2013.01); *G01N 2800/324* (2013.01)

(58) Field of Classification Search
None
See application file for complete search history.

(56) References Cited

U.S. PATENT DOCUMENTS

| 9,175,346 B2 * | 11/2015 | Hanzawa ............. C12Q 1/6883 |
|---|---|---|
| 2013/0040851 A1 | 2/2013 | Hanzawa et al. |
| 2013/0302821 A1 | 11/2013 | Sakamoto et al. |

FOREIGN PATENT DOCUMENTS

| JP | 2011-232218 A | 11/2011 | |
|---|---|---|---|
| JP | 2012-107989 A | 6/2012 | |
| WO | WO 2011136080 A1 * | 11/2011 | ........... C12Q 1/6883 |

OTHER PUBLICATIONS

X. Wang et al., Biomarkers of Vulnerable Atheromatous Plaques: Translational Medicine Perspectives, Advances in Clinical Chemistry, vol. 50, pp. 1-22, 2010.

H. O. Madsen et al., Association of mannose-binding-lectin deficiency with severe atherosclerosis, The Lancet, vol. 352, pp. 959-960, 1998.

* cited by examiner

*Primary Examiner* — Zachary Howard
(74) *Attorney, Agent, or Firm* — Baker Botts L.L.P.

(57) ABSTRACT

It is intended to evaluate an ischemic heart disease with high accuracy by convenient operation. The method for evaluating an ischemic heart disease according to the present invention comprises the steps of: assaying complement factor H and/or complement factor D in a sample derived from the blood of a test subject; and comparing the concentration of the complement factor H and/or the concentration of the complement factor D assayed in the preceding step with a reference value(s), wherein it is determined that the seriousness of the ischemic heart disease is high when the concentration falls below the reference value.

4 Claims, 6 Drawing Sheets

METHOD FOR EVALUATING ISCHEMIC HEART DISEASE BY ASSAYING COMPLEMENT FACTOR H OR D

CLAIM OF PRIORITY

The present application claims priority from Japanese patent application JP 2013-214455 filed on Oct. 15, 2013, the content of which is hereby incorporated by reference into this application.

BACKGROUND OF THE INVENTION

Field of the Invention

The present invention relates to a method, a kit, and an apparatus for evaluating the presence or absence of an ischemic heart disease, for example, stable angina or acute myocardial infarction, and/or the seriousness thereof.

Background Art

The number of patients with heart diseases such as angina pectoris or myocardial infarction is rapidly increasing along with the westernization of diet or the aging society. Such heart diseases are principally caused by rupture of unstable plaques formed in arterial vessels by arteriosclerosis, rapid thrombus formation, and resultingly evoked myocardial ischemia (ischemic heart disease). For the in vitro diagnosis of these heart diseases, traditional risk factors (age, sex, obesity, hyperlipidemia, hypertension, hyperglycemia, and smoking) as well as testing methods using inflammation, vascular endothelial disorder, or a thrombus formation-related factor as an index have been discussed in a large number of epidemiologic studies. Among others, C-reactive protein (CRP) has been studied most frequently as a biomarker and has also been evaluated by large clinical trials. At this time, however, the CRP level alone cannot serve as an index for the risk of an ischemic heart disease. Thus, the challenge to ischemic heart diseases has been to develop a convenient testing method with excellence in quantitative performance and reproducibility using a novel biomarker (Wang X. and Connolly T. M., Advances in Clinical Chemistry, Vol. 50, p. 1-22, 2010).

Previous reports disclosed a method for testing the presence or absence of arteriosclerosis or determining the progression stages, comprising: identifying, by proteome analysis, a protein group whose expression varies with the progression of arteriosclerosis; recording this variation as an expression profile database; and checking variation in protein expression in a sample against the database (JP Patent Publication (Kokai) Nos. 2011-232218 A (2011) and 2012-107989 A (2012)). JP Patent Publication (Kokai) No. 2011-232218 A (2011) has revealed by analysis using mouse models of arteriosclerosis that the expression levels of a group of proteins including complement factor D correlate with the seriousness of arteriosclerotic ischemic heart disease. JP Patent Publication (Kokai) No. 2012-107989 A (2012) has revealed that, since the expression levels of a group of proteins including complement factor H vary at an arteriosclerotic plaque site, the expression levels of these proteins at the arteriosclerotic plaque site (tissue slice) can be assayed to thereby evaluate the seriousness of arteriosclerotic ischemic heart disease.

Figure 6:
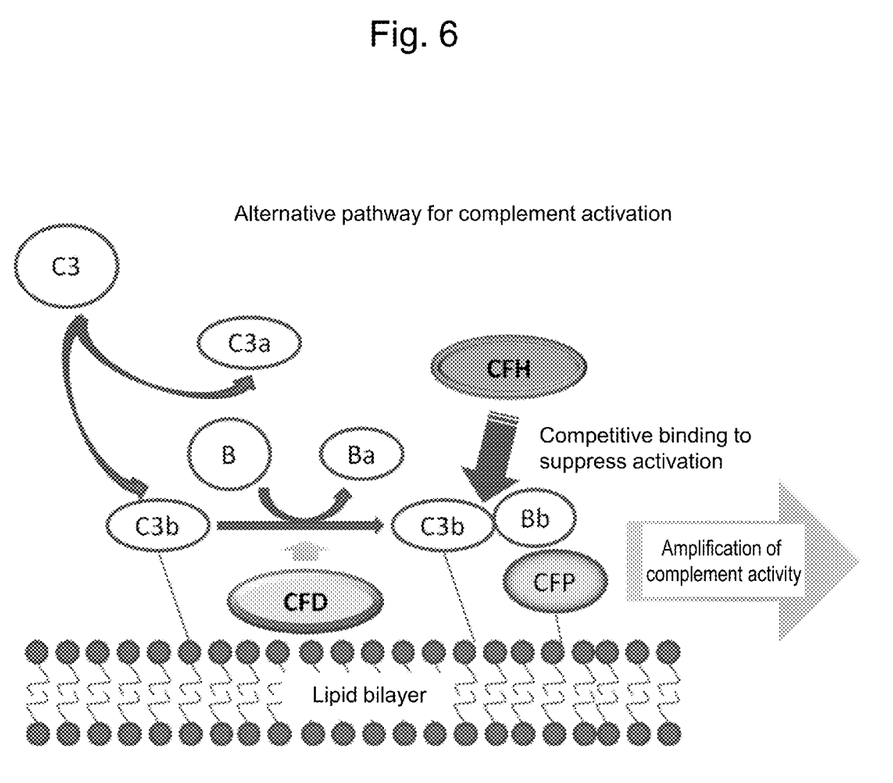
FIG. 6 is a schematic configuration diagram showing the second pathway of complement activation composed of a plurality of complement-related factors.

The complement factor H or the complement factor D is a protein that is involved in immune or inflammatory response and included in a "the complement system" known as one of biological control mechanisms. The complement system is constituted, as shown in FIG. 6, by a group of 20 or more types of proteins (complement factors) present in blood. Complement receptors or complement regulatory membrane factors are found on the surface of blood cells contained in blood or vascular endothelial cells. Upon invasion of pathogens or inflammatory stimulation, these proteins cause a chain reaction, thereby activating complements (or the complement system). Meanwhile, the complement factors as well as regulatory factors perform strict regulation in order to prevent unfavorable "activation" from being out of control. Reportedly, patients genetically deficient in mannose-binding lectin, a complement factor, have an advanced stage of arteriosclerosis and are often affected by heart diseases (Madsen H. O., Videm V., Svejgaard A., Svennevig J. L., and Garred P., Lancet, Vol. 352, p. 959-960, 1998). Nonetheless, much still remains to be learned about the manner in which the complement system is involved in the progression of arteriosclerotic ischemic heart disease and its related diseases.

SUMMARY OF THE INVENTION

As mentioned above, a biomarker that realizes the highly accurate and simple detection of the presence or absence of an ischemic heart disease or the seriousness thereof has been unknown so far, in spite of the results of various studies associated with the diagnosis of ischemic heart diseases. The ischemic heart disease-related biomarker disclosed in JP Patent Publication (Kokai) No. 2011-232218 A (2011) was identified using mouse models of arteriosclerosis. It is thus uncertain whether this biomarker can be applied to humans to be examined. Alternatively, the ischemic heart disease-related biomarker disclosed in JP Patent Publication (Kokai) No. 2012-107989 A (2012) is detected from a tissue slice prepared from an arteriosclerotic plaque site collected from a test subject. Accordingly, the technique disclosed in JP Patent Publication (Kokai) No. 2012-107989 A (2012) disadvantageously requires very complicated operation for the diagnosis of ischemic heart diseases.

Thus, the present invention has been made in light of these situations, and an object of the present invention is to provide a method, a kit, and an apparatus for evaluating an ischemic heart disease which can evaluate the ischemic heart disease with high accuracy by convenient operation.

The present inventors selected healthy volunteers, stable angina patients, and acute myocardial infarction patients, and collected blood samples. Next, the present inventors measured the concentrations of marker candidates in these samples. As a result, the present inventors found that the concentrations of complement factor H and complement factor D in blood significantly decrease as the ischemic heart disease becomes more serious. The present inventors also found that the concentration of the complement factor H positively correlates with the concentration of the complement factor D in blood. From these results, the present inventors obtained findings that complement factor H and/or complement factor D can be used as a biomarker for evaluating the presence or absence of an ischemic heart disease and the seriousness thereof, leading to the completion of the present invention.

The present invention encompasses the following aspects:

(1) A method for evaluating an ischemic heart disease, comprising the steps of: assaying complement factor H and/or complement factor D in a sample derived from the blood of a test subject; and comparing the concentration of the complement factor H and/or the concentration of the complement factor D assayed in the preceding step with a reference value(s), wherein it is determined that the seriousness of the ischemic heart disease is high when the concentration falls below the reference value.

(2) The method for evaluating an ischemic heart disease according to (1), wherein the seriousness of the ischemic heart disease offers information indicating the determination of the presence of the ischemic heart disease in the test subject and the extent of progression of the heart disease present in the test subject.

(3) The method for evaluating an ischemic heart disease according to (1), wherein the step of assaying complement factor H and/or complement factor D comprises quantifying complement factor H and/or complement factor D protein(s) or quantifying mRNA encoding the protein.

(4) The method for evaluating an ischemic heart disease according to (1), wherein the step of assaying complement factor H and/or complement factor D employs a substance specifically binding to complement factor H and/or complement factor D protein(s) or is carried out by mass spectrometry or electrophoresis.

(5) A kit for evaluating an ischemic heart disease, comprising a section that assays complement factor H and/or complement factor D in a sample derived from the blood of a test subject, wherein it is determined that the seriousness of the ischemic heart disease is high when the concentration of the complement factor H and/or the concentration of the complement factor D falls below a reference value(s).

(6) The kit for evaluating an ischemic heart disease according to (5), wherein the section assays complement factor H and/or complement factor D protein(s) or assays mRNA encoding the protein.

(7) The kit for evaluating an ischemic heart disease according to (5), wherein the section is a substance specifically binding to complement factor H and/or complement factor D protein(s).

(8) The kit for evaluating an ischemic heart disease according to (5), wherein the section is an antibody against the complement factor H and/or the complement factor D, the antibody being immobilized on a solid-phase support.

(9) An apparatus for evaluating an ischemic heart disease, comprising: an assay unit that assays complement factor H and/or complement factor D in a sample derived from the blood of a test subject; a comparison unit that compares the concentration of the complement factor H and/or the concentration of the complement factor D assayed in the assay unit with a reference value(s); and a determination unit that determines that the seriousness of the ischemic heart disease is high when the concentration falls below the reference value.

(10) The apparatus for evaluating an ischemic heart disease according to (9), wherein the determination unit determines, as the seriousness of the ischemic heart disease, the presence of the ischemic heart disease in the test subject and the extent of progression of the heart disease present in the test subject.

(11) The apparatus for evaluating an ischemic heart disease according to (9), wherein the assay unit quantifies complement factor H and/or complement factor D protein(s) or quantifies mRNA encoding the protein.

(12) The apparatus for evaluating an ischemic heart disease according to (9), wherein the assay unit employs a substance specifically binding to complement factor H and/or complement factor D protein(s) or performs the assay by mass spectrometry or electrophoresis.

According to the present invention, the presence or absence of an ischemic heart disease and/or the seriousness thereof can be evaluated with high accuracy by convenient operation. Specifically, the method, the kit, and the apparatus for evaluating an ischemic heart disease according to the present invention can evaluate the presence or absence of an ischemic heart disease and the seriousness thereof in a test subject by convenient operation which involves assaying complement factor H and/or complement factor D in a sample derived from blood collected from the test subject. Moreover, the method, the kit, and the apparatus for evaluating an ischemic heart disease according to the present invention can also be used in accurate and convenient examination or analysis on possible development and progression of ischemic heart diseases and disorders caused thereby, the development of various reagents or drugs, or the development of related apparatuses.

DETAILED DESCRIPTION OF THE PREFERRED EMBODIMENTS

In the method, the kit, and the apparatus for evaluating an ischemic heart disease according to the present invention, a novel biomarker is used for evaluating the ischemic heart disease. This biomarker is a protein whose expression level decreases with the progression of the ischemic heart disease, and as such is useful in, for example, the prediction of occurrence of the ischemic heart disease, the determination of the extent of progression, the prediction of prognosis, and the evaluation of efficacy of a therapeutic drug or method for the ischemic heart disease. The novel biomarker is complement factor H and/or complement factor D contained in a blood-derived sample.

In this context, the ischemic heart disease means a disease with myocardial necrosis or depressed cardiac functions resulting from poor blood flow (ischemia) to the heart muscle due to coronary narrowing or occlusion. Particularly, when the coronary narrowing or occlusion is caused by arteriosclerosis, this disease is called arteriosclerotic ischemic heart disease. The biomarker used in the method, the kit, and the apparatus for evaluating an ischemic heart disease according to the present invention is particularly useful in the evaluation of arteriosclerotic ischemic heart disease among ischemic heart diseases.

The ischemic heart disease also includes: angina pectoris including stable angina, unstable angina, and effort angina; myocardial infarction including acute myocardial infarction and old myocardial infarction; and heart failure. These ischemic heart diseases are ranked in order of seriousness as follows: angina pectoris, myocardial infarction, and heart failure, more specifically, stable angina, unstable angina, acute myocardial infarction, old myocardial infarction, and heart failure.

The term "biomarker" means a protein to be assayed for evaluating an ischemic heart disease, i.e., complement factor H and/or complement factor D, or a gene (mRNA) encoding the protein. The term "assaying" means determining the abundance of the protein or the gene (mRNA) encoding the protein in a sample. In the present invention, the phrase "assaying a biomarker" may mean that the biomarker protein or its secondary substance or derivative is assayed or may mean that the expression of the gene (mRNA) encoding the protein is assayed. The "secondary substance" and the "derivative" mean a substance secondarily produced from the biomarker protein and a substance derived from the protein, respectively. Examples of the "secondary substance" and the "derivative" include, but not limited to, signal peptide-containing proteins, particular subunit molecules of proteins, modified proteins, and protein fragments.

The blood-derived sample means blood collected from a test subject for the evaluation of an ischemic heart disease and a sample obtained by the processing of the blood. More specifically, the blood-derived sample includes blood samples, serum samples, and plasma samples. Particularly, in the case of using a plasma sample, EDTA is preferably used as an anticoagulant. Alternatively, an anticoagulant known or generally used in the art, such as heparin or sodium citrate, may be used. A blood sample is preferably cooled in ice or refrigerated after blood collection.

The test subject refers to a human or any of other mammals, for example, primates (monkey, chimpanzee, etc.), livestock animals (cattle, horse, pig, sheep, etc.), pet animals (dog, cat, etc.), and laboratory animals (mouse, rat, rabbit, etc.) and may be a reptile, bird, or the like. The test subject is particularly preferably a human.

The assay of the biomarker means, preferably, the semiquantitative or quantitative determination of the level or concentration thereof in the blood-derived sample. The level may be an absolute level or may be a relative level. This assay can be conducted directly or indirectly. The direct assay involves determining the level or concentration thereof on the basis of a signal correlating directly with the number of biomarker protein or mRNA molecules present in the sample. Such a signal is based on, for example, the particular physical or chemical properties of the protein or the mRNA. The indirect assay refers to the measurement of a signal generated from a secondary component (i.e., a component other than the marker protein or mRNA), for example, a ligand (e.g., antibody), a label, or an enzyme reaction product.

According to one embodiment of the present invention, the protein used as the biomarker can be assayed by means of a section that assays the level of the protein in the sample. Such a section is known in the art and includes, for example, immunoassay methods and reagents. Alternatively, the protein used as the biomarker can be assayed by means of a section that assays physical or chemical properties unique to the protein, for example, a section that assays the accurate molecular weight or NMR spectrum thereof. Examples of the section that assays the protein include analyzing apparatuses such as biosensors, protein chips, optical apparatuses connected to immunoassay, mass spectrometers, NMR analyzers, two-dimensional electrophoresis apparatuses, and chromatography apparatuses. These analyzing apparatuses may each be used alone to assay the biomarker or may be used in combination of two or more thereof to assay the biomarker.

According to a preferred embodiment, the protein used as the biomarker can be assayed by immunoassay (immunological determination method). Specifically, the biomarker is assayed on the basis of the reaction of the protein in the blood-derived sample with an antibody specifically binding to the protein. A method generally used in the art can be used as the immunoassay without limitations. The immunoassay may be carried out, for example, in any of liquid-phase and solid-phase systems. Immunoassay in a solid-phase system is preferably used in terms of easy detection. The immunoassay is not limited by its format and may be a direct solid-phase method or any of other methods such as sandwich, competition, Western blotting, and ELISA (enzyme linked immunosorbent assay) methods.

In this context, the antibody against the biomarker protein may be any of monoclonal and polyclonal antibodies or may be a fragment such as Fab or Fv capable of binding to an epitope in the biomarker protein. Primary and secondary antibodies may be used in the biomarker assay. In such a case, monoclonal antibodies can be used as both of the antibodies. Alternatively, a polyclonal antibody may be used as either of the primary or secondary antibody. These antibodies can be prepared by a method known in the art or may be obtained as commercially available products.

The binding between the biomarker protein and the antibody can be measured according to a well-known method. The method for measuring the binding between the biomarker protein and the antibody is not particularly limited, and an effective and optimum measurement method for each assay can be determined according to the type and format of the immunoassay adopted, the type of the label used, etc. For example, the binding of the antibody to the biomarker in the blood-derived sample can be easily detected by the direct detection of the binding on the basis of the label on the antibody or by the indirect detection thereof using a labeled secondary antibody, a biotin-avidin complex, or the like.

In the case of selecting a solid-phase system for the immunoassay, for example, a protein component in the blood-derived sample can be immobilized on a solid phase. In such a case, the method that can be adopted comprises the steps of, for example, (1) preparing protein components from the blood-derived sample, (2) fractionating the protein components by SDS-polyacrylamide gel electrophoresis, (3) transferring the protein on the gel to a solid phase, (4) reacting therewith an antibody (primary antibody) specifically binding to the biomarker protein, (5) washing the solid phase, (6) bringing the solid phase into contact with a labeled antibody (secondary antibody) specifically binding to the primary antibody, (7) washing the solid phase, and (8) assaying the biomarker on the basis of the label. Alternatively, the antibody specifically binding to the biomarker protein may be immobilized on a solid phase. This method is a so-called "sandwich method" and is widely used as "ELISA", which employs an enzyme as the label. Such a solid-phase method is preferred for detection of the protein in a very small amount and convenient operation.

For the solid-phase system, the antibody specifically binding to the biomarker protein or the protein component in the sample is immobilized on a solid phase (plate, membrane, beads, etc.), and the immunological binding between the biomarker and the antibody is tested on this solid phase. A solid phase routinely used in the art can be used without limitations. For example, a commercially available nitrocellulose membrane or PVDF membrane can be used. Such solid-phase immobilization of the antibody or the protein component in the sample enables easy removal of unbound sample components or reagents. Particularly, a protein array method using a membrane with dozens of types of antibodies immobilized thereon can analyze the expression of many types of marker proteins in a short time using a small amount of a test subject-derived sample (plasma, etc.). Such immunoassay can also be carried out by use of, for example, a test strip, which renders operation convenient. In short, the protein array method using a membrane with dozens of types of antibodies immobilized thereon can be applied to the method, the kit, and the apparatus for evaluating an ischemic heart disease.

In the case of selecting a liquid-phase system for the immunoassay, for example, the sample is brought into contact with a labeled antibody, which is then allowed to bind to the biomarker protein, and the resulting complex is separated, followed by the detection of a signal from the label. Alternatively, the blood-derived sample may be brought into contact with an antibody (primary antibody) against the biomarker protein, which is then allowed to bind to the biomarker protein, and a labeled antibody (secondary antibody) is allowed to bind to the resulting complex. A signal from the label on this tripartite complex can be detected. Alternatively, in order to further enhance the signal, an unlabeled secondary antibody may be first allowed to bind to an antibody-marker protein complex, and a labeling material can be allowed to bind to this secondary antibody. Such binding of the labeling material to the secondary antibody can be carried out, for example, by the biotinylation of the secondary antibody and the attachment of avidin to the labeling material.

An enzyme, a radioisotope, a fluorescent dye, or an avidin-biotin system can be used as the label for labeling the antibody for use in the immunoassay. An enzyme for use in usual enzyme immunoassay (EIA), for example, peroxidase, β-galactosidase, or alkaline phosphatase, can be used as the enzyme. Alternatively, an enzyme inhibitor, a coenzyme, or the like may be used. The binding between any of these enzymes and the antibody can be carried out by a method known in the art using a cross-linking agent such as a maleimide compound. A radioisotope for use in usual radioimmunoassay (RIA), for example, $^{125}$I or $^{3}$H, can be used as the radioisotope. A fluorescent dye for use in a usual fluorescence antibody technique, for example, fluorescein isothiocyanate (FITC) or tetramethylrhodamine isothiocyanate (TRITC), can be used as the fluorescent dye.

In the case of using a biotin-avidin complex system, the sample is reacted with a biotinylated antibody, and the resulting complex is reacted with label-attached avidin. Since avidin is capable of specifically binding to biotin, a signal from the label attached to avidin can be detected to thereby assay the binding between the antibody and the marker protein. The label to be attached to avidin is not particularly limited and is preferably, for example, an enzyme label (peroxidase, alkaline phosphatase, etc.).

The detection of the signal from the label can also be carried out according to a method known in the art. In the case of using, for example, an enzyme label, a substrate that is degradable by the action of the enzyme to develop color is added to the reaction system. The amount of the substrate degraded is optically measured to thereby determine enzyme activity, which is then converted to the amount of the bound antibody. The amount of the antibody is calculated by comparison with a standard value. The substrate differs depending on the type of the enzyme used. For example, when peroxidase is used as the enzyme, 3,3',5,5'-tetramethylbenzidine can be used. When alkaline phosphatase is used as the enzyme, p-nitrophenol or the like can be used. In the case of using a radiolabel, the amount of radiation emitted by the radiolabel is measured using a scintillation counter or the like. A fluorescent label can be detected and quantified using, for example, a fluorescence microscope or a plate reader.

In the method, the kit, and the apparatus for evaluating an ischemic heart disease according to the present invention, the biomarker can be assayed by means of a section that assays the level of biomarker protein-encoding mRNA contained in the blood-derived sample. Such a section is not particularly limited, and any approach known in the art can be used. Examples of such a section include primer DNA or probe DNA comprising the whole or partial sequence of DNA encoding the protein, or its complementary sequence. The primer DNA or the probe DNA specifically binds to the protein-encoding mRNA contained in the blood-derived sample collected from the test subject, or cDNA corresponding to the mRNA.

The primer DNA and the probe DNA can be easily designed using a program known in the art on the basis of the nucleotide sequence of the DNA encoding the biomarker protein and can be prepared according to a method generally known to those skilled in the art.

In order to assay the biomarker mRNA contained in the blood-derived sample collected from the test subject, the primer DNA and/or the probe DNA is used in amplification reaction or hybridization reaction, respectively, and the resulting amplification product or hybrid is detected. For such reaction, the mRNA or the cDNA corresponding to the mRNA is usually prepared from the test subject-derived sample by use of a method well known in the art. For example, a guanidine-cesium chloride ultracentrifugation method, a hot phenol method, or an acid guanidinium thiocyanate-phenol-chloroform (AGPC) method can be used in RNA extraction. The cDNA can be prepared by use of reverse transcriptase known in the art. The sample thus prepared is subjected to amplification reaction and/or hybridization reaction given below.

Amplification reaction with the mRNA or the cDNA as a template is performed using the primer DNA. The specific amplification reaction can be detected to thereby assay the biomarker mRNA contained in the blood-derived sample. Examples of the amplification approach can include, but not particularly limited to, methods known in the art based on the principles of polymerase chain reaction (PCR) (PCR, RT-PCR, real-time PCR, etc.). The amplification product can be detected by means of a section known in the art capable of specifically recognizing the amplification product obtained from the amplification reaction. The presence or absence of a successfully amplified fragment having a particular size can be confirmed by use of for example, agarose gel electrophoresis, to thereby detect the specific amplification reaction.

Alternatively, a label such as a radioisotope, a fluorescent material, or a luminescent material may be allowed to act on dNTP that is incorporated during the process of amplification reaction. This label can be detected. For example, $^{32}$P, $^{125}$I, or $^{35}$S can be used as the radioisotope. For example, fluorescein isothiocyanate (FITC), sulforhodamine (SR), or tetramethylrhodamine isothiocyanate (TRITC) can be used as the fluorescent material. For example, luciferin can be used as the luminescent material. The label is not particularly limited by its type, introduction method, etc., and various conventionally known approaches can be used.

Examples of the label introduction method include random priming methods using radioisotopes.

The labeled dNTP-incorporated amplification product can be observed by any method known in the art for detecting the label mentioned above. In the case of using, for example, a radioisotope as the label, its radioactivity can be measured using, for example, a liquid scintillation counter or a γ-counter. In the case of using a fluorescent label, its fluorescence can be detected using, for example, a fluorescence microscope or a fluorescence plate reader.

Alternatively, the hybridization reaction of the sample may be performed using the probe DNA, and its specific binding (hybrid) can be detected to thereby assay the biomarker mRNA contained in the blood-derived sample. The hybridization reaction is performed under conditions that permit only the specific binding of the probe DNA to the biomarker mRNA contained in the blood-derived sample or cDNA synthesized from the mRNA, i.e., under stringent conditions. For the hybridization, an appropriate label such as a fluorescent label (fluorescein, rhodamine, etc.), a radiolabel ($^{32}P$, etc.), or a biotin label can be attached to the probe DNA.

The detection using the labeled probe DNA involves bringing the probe DNA into contact with the sample or the mRNA or cDNA prepared therefrom such that the probe DNA can be hybridized thereto. Specifically, the sample or the mRNA or cDNA is immobilized on an appropriate solid phase, and the labeled probe DNA is added thereto. Alternatively, the labeled probe DNA is immobilized on an appropriate solid phase, and the sample or the mRNA or cDNA is added thereto. As a result, the probe DNA is brought into contact with the sample or the mRNA or cDNA to perform hybridization reaction. After removal of unhybridized probe DNA, the label on the probe DNA hybridized with the sample or the mRNA or cDNA is detected. When the label is detected, the mRNA encoding the biomarker protein is expressed in the blood-derived sample. Examples of the assay method using the labeled probe DNA can include Southern hybridization and Northern hybridization.

In this way, the biomarker contained in the blood-derived sample collected from the test subject is assayed. On the basis of the results, an ischemic heart disease in the test subject can be evaluated. In the present specification, the "evaluation of an ischemic heart disease" is meant to include the determination of the presence of the ischemic heart disease in the test subject and the determination of the extent of progression (seriousness) of the ischemic heart disease present in the test subject. Such evaluation of an ischemic heart disease in the test subject can also be used for evaluating therapeutic effects on the ischemic heart disease present in the test subject and for predicting the prognosis of the ischemic heart disease present in the test subject. In the present invention, the "evaluation" also encompasses the continuous monitoring of an already evaluated or diagnosed ischemic heart disease, and the validation of already conducted evaluation or diagnosis of an ischemic heart disease.

The "evaluation" using the method, the kit, and the apparatus for evaluating an ischemic heart disease according to the present invention is intended to be able to evaluate a statistically significant ratio of test subjects. Accordingly, the "evaluation" using the method, the kit, and the apparatus for evaluating an ischemic heart disease according to the present invention may not always produce correct results for all (i.e., 100%) of test subjects to be evaluated. The statistically significant ratio can be determined by use of various well known statistical evaluation tools, for example, determination of a confidence interval, determination of a p value, Student's t test, or Mann-Whitney test. The confidence interval is preferably at least 90%. The p value is preferably 0.1, 0.01, 0.005, or 0.0001. More preferably, the method, the kit, and the apparatus for evaluating an ischemic heart disease according to the present invention can properly evaluate at least 60%, at least 80%, or at least 90% of the test subjects.

Specifically, the exemplary evaluation of an ischemic heart disease comprises: assaying complement factor H and/or complement factor D in a sample derived from the blood of a test subject; and comparing, for example, the concentration of the complement factor H and/or the concentration of the complement factor D with their respective reference values.

When either or both of the complement factor H concentration and the complement factor D concentration are lower than their respective reference values, the test subject is found likely to have the ischemic heart disease. Particularly, when both of the complement factor H concentration and the complement factor D concentration are lower than their respective reference values, the test subject is found more likely to have the ischemic heart disease. On the contrary, when both of the complement factor H concentration and the complement factor D concentration are equal to or higher than their respective reference values, the test subject is found likely to have no ischemic heart disease.

In this context, in the case of using plasma as the blood-derived sample, the reference value of the complement factor H concentration can be 320 µg/ml and is preferably 560 µg/ml, more preferably 680 µg/ml. Likewise, the reference value of the complement factor D concentration can be 2.1 µg/ml and is preferably 2.7 µg/ml, more preferably 3.0 µg/ml. The reference value is not particularly limited to those described above. For example, the numerical value of the reference value can be appropriately modified by increasing the number of blood-derived samples that serve as a basis for the calculation of the reference value.

In addition, the seriousness of the ischemic heart disease can be evaluated on the basis of the concentration of the complement factor H and/or the concentration of the complement factor D. When either or both of the complement factor H concentration and the complement factor D concentration are lower than their respective reference values lower than the reference values mentioned above, the test subject is found likely to have an advanced stage of the ischemic heart disease. In this context, in the case of using plasma as the blood-derived sample for evaluating the seriousness of the ischemic heart disease, the reference value of the complement factor H concentration can be 260 µg/ml and is preferably 450 µg/ml, more preferably 510 µg/ml. Likewise, the reference value of the complement factor D concentration can be 1.3 µg/ml and is preferably 1.9 µg/ml, more preferably 2.2 µg/ml. The reference value is not particularly limited to those described above. For example, the numerical value of the reference value can be appropriately modified by increasing the number of blood-derived samples that serve as a basis for the calculation of the reference value.

The method for evaluating an ischemic heart disease may be carried out in combination with an additional conventionally known method for diagnosing an ischemic heart disease. Examples of such a conventionally known method for diagnosing an ischemic heart disease include the assay of physiological and biochemical heart disease markers (e.g., hypertension, cholesterol level, or triglyceride level), electrocardiography, pulse wave velocity (PWV) measurement, and angiography.

The method for evaluating an ischemic heart disease according to the present invention permits early detection of the occurrence of the ischemic heart disease. Specifically, the method for evaluating an ischemic heart disease according to the present invention can determine the presence of an early-stage ischemic heart disease, which cannot be recognized by the conventionally known method for diagnosing an ischemic heart disease. In addition, the method for evaluating an ischemic heart disease according to the present invention can determine the extent of progression (seriousness) of the ischemic heart disease, if present. This allows the test subject to receive early treatment of the ischemic heart disease and appropriately-timed, proper treatment for the progression of the disease. Particularly, the method for evaluating an ischemic heart disease according to the present invention can evaluate the ischemic heart disease by use of the blood-derived sample and as such, can advantageously achieve rapid and simple evaluation compared with the conventional method.

The method for evaluating an ischemic heart disease according to the present invention can be carried out easily and conveniently by use of an evaluation kit and/or an evaluation apparatus comprising a section that assays a biomarker (concentration of complement factor H and/or complement factor D).

The evaluation kit comprises a section that assays complement factor H and/or complement factor D in a sample derived from the blood of a test subject. One example of the evaluation kit is a reagent set for immunoassay which is constituted by an antibody reagent against each biomarker protein, a buffer solution for dilution or washing, a standard antigen, a labeled antibody reagent specifically binding to each antibody reagent, a substrate reagent that develops color, luminescence, or fluorescence, a manual that states procedures and an evaluation method, etc. The antibody contained in the evaluation kit may be labeled in advance or may not be labeled. Also, this antibody may be immobilized on a solid-phase support (e.g., membrane or beads).

The evaluation kit may comprise an instruction that states procedures and protocols for carrying out the method for evaluating an ischemic heart disease, a table indicating reference values or reference ranges for use in the evaluation, etc.

The components contained in the evaluation kit may be provided individually or may be provided in a single container. Preferably, the evaluation kit comprises all of components necessary for carrying out the method for evaluating an ischemic heart disease such that these components can be immediately used, for example, with their concentrations adjusted.

Figure 1:
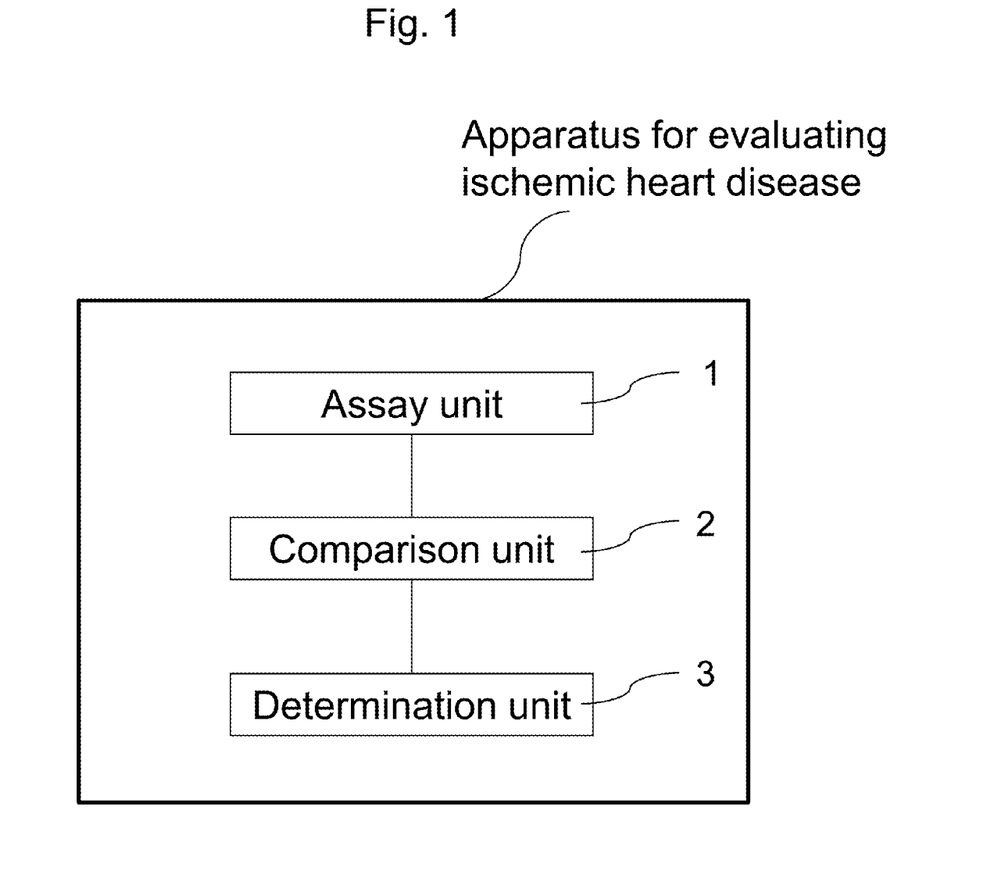
FIG. 1 is a schematic configuration diagram showing one example of the apparatus for evaluating an ischemic heart disease according to the present invention.

The apparatus for evaluating a heart disease according to the present invention comprises, as shown in FIG. 1, assay unit 1 that assays complement factor H and/or complement factor D in a sample derived from the blood of a test subject, comparison unit 2 that compares the concentration of the complement factor H and/or the concentration of the complement factor D assayed in the assay unit 1 with a reference value(s), and determination unit 3 that determines that the seriousness of the ischemic heart disease is high when the concentration falls below the reference value.

In this context, the assay unit 1 comprises, as mentioned above, a section that assays the level of the protein used as the biomarker in the blood-derived sample, or a section that assays the level of mRNA encoding the protein. The assay unit 1 comprises, as mentioned above, any of analyzing apparatuses such as biosensors, protein chips, optical apparatuses connected to immunoassay, mass spectrometers, NMR analyzers, two-dimensional electrophoresis apparatuses, and chromatography apparatuses, for the protein analyte. On the other hand, the assay unit 1 comprises, as mentioned above, any of detection apparatuses such as a liquid scintillation counter, a γ-counter, a fluorescence microscope, and a fluorescence plate reader, for the nucleic acid analyte.

The assay unit 1 comprises a data analysis unit composed of software and a calculator for processing measurement values obtained from the aforementioned analyzing apparatus or the like. The data analysis unit calculates the concentration of the complement factor H and/or the concentration of the complement factor D in the blood-derived sample with reference to data such as a calibration curve on the basis of the measurement values obtained from the aforementioned analyzing apparatus or the like. The data analysis unit can comprise, for example, a signal display portion, an analysis unit for the measurement values, and a computer unit.

The comparison unit 2 reads out each of a reference value relating to the concentration of the biomarker complement factor H and a reference value relating to the concentration of the biomarker complement factor D from a memory or the like, and compares the concentration of the complement factor H and/or the concentration of the complement factor D assayed in the assay unit with these reference values. In this case, the comparison unit 2 selects and reads out appropriate reference values according to the type (i.e., blood, serum, or plasma) of the blood-derived sample.

The determination unit 3 determines that the seriousness of the ischemic heart disease is high on the basis of the results of comparing the concentration of the complement factor H and/or the concentration of the complement factor D with their respective reference values in the comparison unit 2, when the concentration falls below the reference value. In this context, the determination unit 3 gains, as the seriousness, information indicating that the test subject is highly suspected of having the ischemic heart disease, and/or information indicating the extent of progression of the ischemic heart disease present in the test subject.

As mentioned above, the biomarker according to the present invention can be used for evaluating the efficacy of a therapeutic drug or method for the ischemic heart disease or for screening therapeutic drug candidates for the ischemic heart disease. Specifically, the method for evaluating the efficacy of a therapeutic drug or method for the ischemic heart disease or the method for screening therapeutic drug candidates for the ischemic heart disease comprises the steps of:

(a) assaying the expression of complement factor H in a sample from an animal with a heart disease treated with a therapeutic drug or method to be tested; and (b) evaluating the efficacy of the therapeutic drug or method to be tested on the heart disease on the basis of the results of the step (a).

The animal subject may be a human having the ischemic heart disease or may be an animal model (mouse, rat, rabbit, etc.) of the ischemic heart disease. In general, the efficacy of the therapeutic drug or method to be tested is confirmed in animal models and then evaluated in humans by, for example, clinical trials.

The therapeutic drug or method to be tested by evaluation or screening is not particularly limited by its type. Examples of the therapeutic drug or method to be tested can include arbitrary physical factors, specifically: naturally occurring molecules such as amino acids, peptides, oligopeptides, polypeptides, proteins, nucleic acids, lipids, carbohydrates (sugars, etc.), steroids, glycopeptides, glycoproteins, and proteoglycans; synthetic analogs or derivatives of the naturally occurring molecules, such as pseudopeptides and nucleic acid molecules (aptamers, antisense nucleic acids, double-stranded RNA (RNAi), etc.); non-naturally occurring molecules such as low-molecular-weight organic compounds (inorganic and organic compound libraries, combinatorial libraries, etc.); and mixtures thereof. The therapeutic drug or method may be a single substance or may be a complex, food, diet, or the like constituted by a plurality of substances. The therapeutic drug or method to be tested may be radiation, UV rays, or the like, in addition to the physical factors as described above.

The treatment of the animal with the therapeutic drug or method to be tested differs depending on the type of the therapeutic drug or method and can be readily determined by those skilled in the art. For example, the administration conditions (e.g., dose, dosing period, and administration route) of the therapeutic drug to be tested can be appropriately determined by those skilled in the art.

Alternatively, the efficacy of the therapeutic drug or method to be tested may be studied under several conditions. Examples of such conditions include the treatment times or periods of the therapeutic drug or method to be tested, the amounts (larger and small) thereof, and the numbers of treatment rounds. For example, a dilution series of the therapeutic drug to be tested can be prepared to thereby establish a plurality of doses.

A plurality of therapeutic drugs or methods to be tested may be used in combination for studying their additive effects, synergistic effects, etc.

The biomarker in a blood-derived sample collected from the animal thus treated with the therapeutic drug or method to be tested is assayed, and its concentration can be compared with that before the treatment to thereby evaluate whether or not the therapeutic drug or method to be tested is effective for improving the ischemic heart disease or for hindering or slowing down the progression of the ischemic heart disease.

In this way, the method for evaluating the efficacy of a therapeutic drug or method for the ischemic heart disease according to the present invention can find a therapeutic drug or method for treatment or prevention of the ischemic heart disease and can further confirm the efficacy of the therapeutic drug or method.

EXAMPLES

Hereinafter, the present invention will be described in more detail with reference to Examples. However, the technical scope of the present invention is not intended to be limited by Examples below. It is obvious to those skilled in the art that various embodiments based on the ideas of the present invention described herein can be made.

Much still remains to be learned about the mechanism of action of the complement system on the progression of ischemic heart diseases. Thus, in the present Examples, the concentrations of complement factor H (CFH) and complement factor D (CFD) on an "alternative pathway" in the complement activation pathway (see FIG. 6) were measured in blood and studied for their relation to the occurrence of ischemic heart diseases and the seriousness thereof. For comparison, complement factor P (CFP) was also studied for its relation to the occurrence of ischemic heart diseases and the seriousness thereof.

[Material and Method]

Materials and methods given below were used in the experiments disclosed herein.

Of arteriosclerotic ischemic heart disease (stable angina or acute myocardial infarction) patients, male patients ranging in age from 45 to less than 75 years old were subjected to blood collection by their consent. Likewise, of healthy volunteers, male patients ranging in age from 45 to less than 75 years old were subjected to blood collection by their consent. Blood was collected into a vacuum blood collection tube (for plasma preparation using EDTA-2Na; VP-NA050KN, Terumo Corp.) per sample. Immediately thereafter, plasma was separated and cryopreserved at −80° C.

The concentrations of CFH, CFD, and CFP in each sample were measured using commercially available ELISA kits. A human CFH detection kit manufactured by USCN Life Science Inc. (E90635HU, USCN Life Science Inc.) was used in the CFH assay. A human CFD detection kit manufactured by R&D Systems, Inc. (Quantikine, DFD00, R&D Systems, Inc.) was used in the CFD assay. A human CFP detection kit manufactured by USCN Life Science Inc. (E90783HU, USCN Life Science Inc.) was used in the CFP assay. Each measurement was carried out according to the instruction manual included in the kit. In order to understand errors among the experiments, pool serum for accuracy control (Consela, Nissui Pharmaceutical Co., Ltd.) was inevitably used in each assay.

Statistical analysis was indicated by mean±standard deviation (SD). The P value was calculated by use of the one-sided Student's t-test.

Table 1 shows the profiles of the test subjects.

TABLE 1

| Test subject | Low-risk group* (n = 25) | Stable angina group (n = 51) | Acute myocardial infarction group (n = 50) |
|---|---|---|---|
| Age (years old) | 58±8.2 | 65.9±6.9 | 61.8±8.5 |
| Sex | Male | Male | Male |
| Systolic blood pressure (mmHg) | 123.6±10.4 | 141.2±24.9 | 128.7±17.6 |
| BMI (%) | 22.2±1.7 | 24±3.3 | 24.7±3.2 |
| Blood glucose level (mg/dL) | 94.5±6.9 | 130.8±40.4 | 156.2±54.8 |
| Smoking history | 5 (20.0%) | 41 (80.4%) | 26 (52.0%) |
| Total cholesterol (mg/dL) | 198.8±34.9 | 161.8±36.7 | 190.4±37.7 |
| LDL cholesterol (mg/dL) | 117±35.8 | 94.9±32.7 | 122.5±34.7 |
| HDL cholesterol (mg/dL) | 55±12.7 | 46.8±12.7 | 48.9±12.2 |
| Triglyceride (mg/dL) | 125.4±118.4 | 128.9±60.3 | 159.7±187 |
| High-sensitive CRP (ng/mL) | 700±600 | 1700±2000 | 2700±9500 |

*Low-risk group: from among healthy volunteers, samples were extracted which satisfied (1) having one or less of 5 heart disease risk factors (hypertension, obesity, hyperglycemia, smoking, and hyperlipidemia), (2) no abnormal finding observed in the heart by electrocardiography, X-ray examination, etc., and (3) no medication (therapeutic drug for hyperlipidemia, antihypertensive, or therapeutic drug for diabetes mellitus).

The results of assaying CFH, CFD, and CFP are shown in Table 2. The average CFH concentration in blood gradually decreased from the low-risk group to the stable angina group and exhibited the lowest value in the acute myocardial infarction group having the most advanced ischemic heart disease. The average CFD concentration in blood, as with CFH, gradually decreased among the low-risk group, the stable angina group, and the acute myocardial infarction group according to the stage of progression of the ischemic heart disease. In contrast to these CFH and CFD variations, CFP was kept constant among the low-risk group, the stable angina group, and the acute myocardial infarction group, regardless of the stage of progression of the ischemic heart disease.

TABLE 2

|  | Low-risk group | Stable angina group | Acute myocardial infarction group |
|---|---|---|---|
| CFD (μg/ml) | 3.3±0.6[1]<br>18[2] | 2.5±0.6<br>18 | 2.2±0.6<br>26 |
| CFH (μg/ml) | 794.8±239.2<br>14 | 637.8±189.3<br>23 | 454.3±141.9<br>13 |
| CFP (μg/ml) | 62±14.6<br>8 | 61.4±8.2<br>10 | 55.6±9.3<br>10 |

[1] Mean ± standard deviation,
[2] the number of samples

Figure 2:
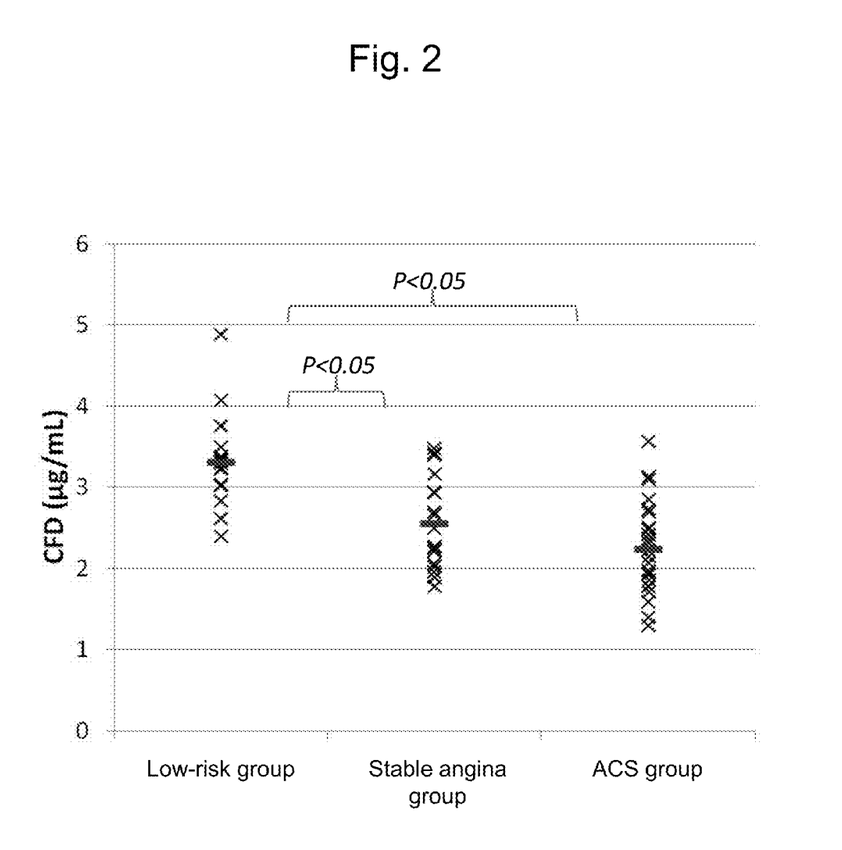
FIG. 2 is a characteristic diagram showing results of measuring CFH concentrations in blood in a low-risk group, a stable angina group, and an acute myocardial infarction group.

FIG. 2 shows the concentration distribution of CFD. As a result of statistical analysis, significant difference was found between the low-risk group and the stable angina group ($p=3.18\times10^{-4}$) and between the low-risk group and the acute myocardial infarction group (referred to as ACS group) ($p=2.01\times10^{-7}$), whereas no significant difference was found between the stable angina group and the acute myocardial infarction group ($p=7.06\times10^{-2}$).

Figure 3:
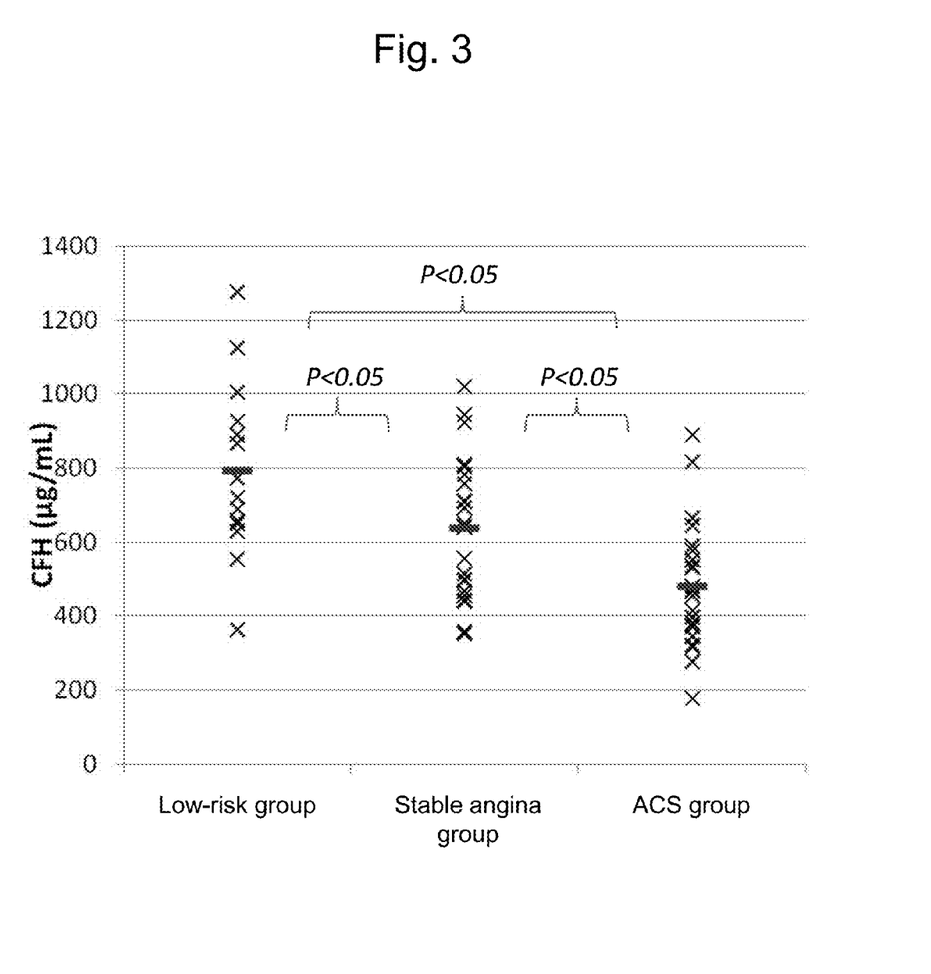
FIG. 3 is a characteristic diagram showing results of measuring CFD concentrations in blood in a low-risk group, a stable angina group, and an acute myocardial infarction group.

FIG. 3 shows the concentration distribution of CFH. As a result of statistical analysis, significant difference was found among the groups (low-risk group vs stable angina group; $p=3.35\times10^{-2}$, low-risk group vs acute myocardial infarction group; $p=1.90\times10^{-5}$, stable angina group vs acute myocardial infarction group; $p=3.16\times10^{-3}$).

Figure 4:
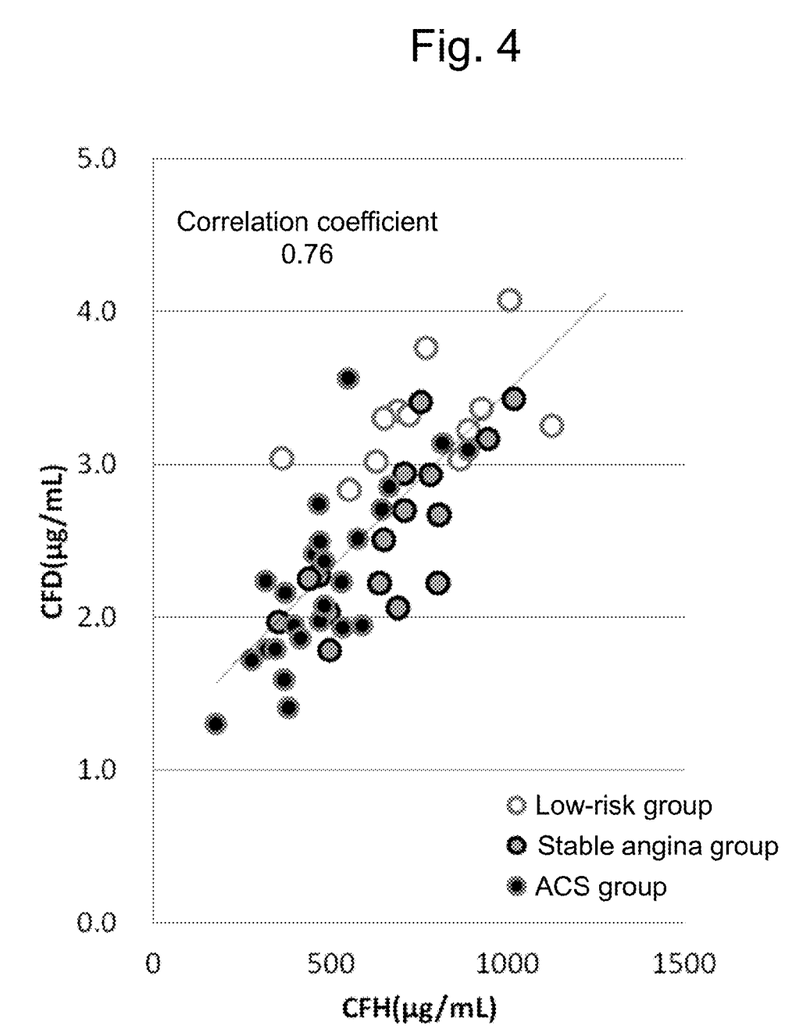
FIG. 4 is a characteristic diagram showing the correlation between the concentrations of CFD and CFH in blood in each sample.

FIG. 4 shows the correlation between the concentrations of CFD and CFH in blood in each sample. As a result of analysis, the concentrations of CFD and CFH in blood were found to exhibit positive correlation (correlation coefficient: 0.76). By contrast, the concentration of CFD or CFH in blood did not correlate with that of the high-sensitive CRP (data not shown).

These results demonstrated that the concentrations of the complement-related factors CFH and CFD in blood serve as indexes for discriminating ischemic heart diseases from the low-risk group. Accordingly, for example, respective reference values are established for the concentrations of CFH and CFD in blood. CFH alone or CFD alone, or both CFH and CFD are assayed, and their concentrations can be compared with their respective reference values to thereby gain information effective for the diagnosis of ischemic heart diseases.

Since the concentration of CFH in blood gradually decreases according to the progression of ischemic heart diseases, a reference value for distinction between the low-risk group and the stable angina group as well as a reference value for discrimination between the stable angina and the acute myocardial infarction group can be established. Then, the concentration of CFH in blood can be measured and compared with these reference values to thereby gain information effective for the diagnosis of the presence or absence of the ischemic heart diseases and the seriousness thereof. The concentrations of CFH and CFD in blood well correlated with each other (FIG. 4). The measurement of either concentration in blood was therefore found to suffice for the stratification of the diseases.

Figure 5:
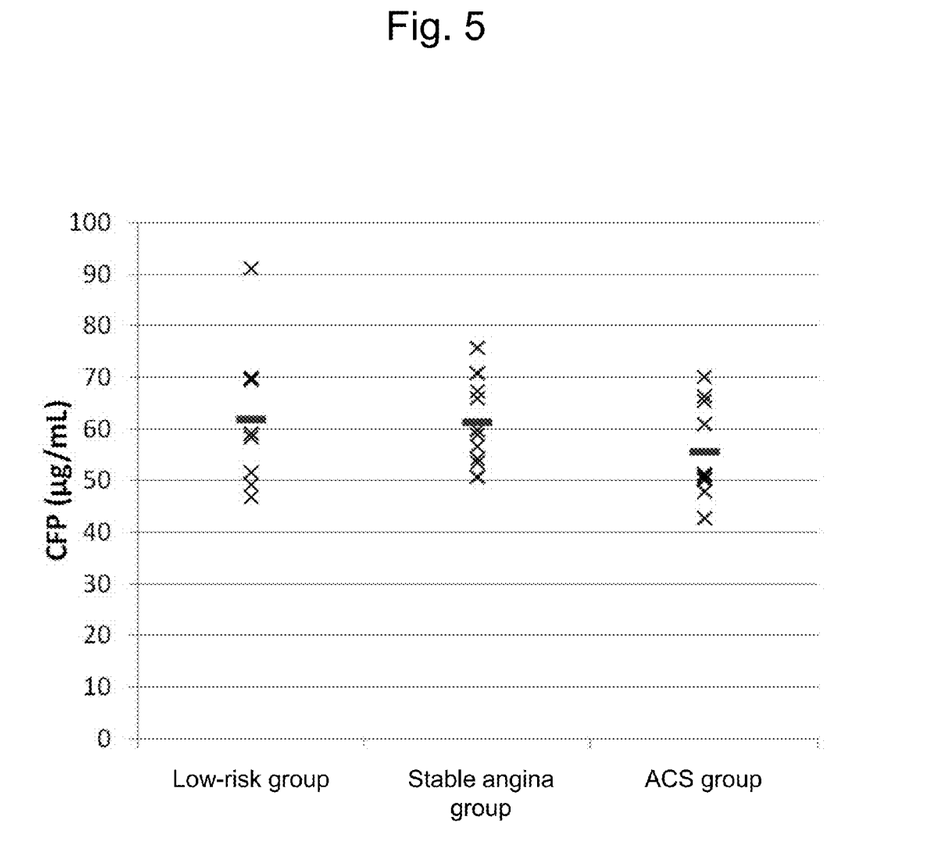
FIG. 5 is a characteristic diagram showing results of measuring CFP concentrations in blood in a low-risk group, a stable angina group, and an acute myocardial infarction group.

The relation of the concentrations of CFD and CFH in blood to ischemic heart diseases differed from that of known blood markers (e.g., high-sensitive CRP) conventionally used as indexes for arteriosclerosis and its related diseases, suggesting that the measurement values of CFD and CFH concentrations in blood are useful as novel markers. As for CFP, which is a complement-related factor as with CFD and CFH, no significant difference was observed between the CFP concentration in blood and ischemic heart diseases, as shown in FIG. 5. From this result, it can be understood that, not the activation or inactivation of the second pathway of complement activation (FIG. 6) composed of a plurality of complement-related factors, but the CFD and CFH concentrations in blood are specifically associated with the presence or absence of ischemic heart diseases and the stage of progression thereof.

The technical scope of the present invention is described herein in detail. However, it is apparent that those skilled in the art may carry out the invention in a scope other than that described above or in Examples. Many changes and modifications can therefore be made in the matters specifying the claimed invention, and such changes and modifications also fall within the scope of the claimed invention.

The present invention provides a technique of predicting the presence or absence of ischemic heart diseases and the progression thereof. According to the present invention, the presence or absence of ischemic heart diseases and the status or the extent of progression thereof can be conveniently determined Thus, the present invention is useful in the field of prevention or treatment of ischemic heart diseases.

What is claimed is:

1. A method for evaluating an ischemic heart disease, comprising the steps of:
    assaying a first concentration of complement factor H or a first concentration comprising complement factor H and complement factor D in a sample derived from the blood of a test subject;
    comparing the first concentration assayed in the preceding step with a reference value(s); and
    determining the presence of the ischemic heart disease when the first concentration falls below the reference value;
    administering a therapeutic drug or method to the test subject;
    assaying a second concentration of complement factor H or a second concentration comprising complement factor H and complement factor D in a second sample derived from the blood of the test subject after the administering of the therapeutic drug or method;
    comparing the second concentration with the first concentration; and
    determining an efficacy of the therapeutic drug or method for the ischemic heart disease based on the comparison.

2. The method for evaluating an ischemic heart disease according to claim 1, further comprising an additional step of determining the extent of progression of the heart disease present in the test subject by comparison of the first concentration with the reference value(s).

3. The method for evaluating an ischemic heart disease according to claim 1, wherein the step of assaying complement factor H or complement factor H and complement factor D comprises quantifying complement factor H or complement factor H and complement factor D protein(s) or quantifying mRNA encoding the protein(s).

4. The method for evaluating an ischemic heart disease according to claim 1, wherein the step of assaying complement factor H or complement factor H and complement factor D employs a substance specifically binding to complement factor H or complement factor H and complement factor D protein(s) or is carried out by mass spectrometry or electrophoresis.

* * * * *